US008846343B2

(12) United States Patent
Akada et al.

(10) Patent No.: US 8,846,343 B2
(45) Date of Patent: Sep. 30, 2014

(54) HIGH-EXPRESSION PROMOTER DERIVED FROM *KLUYVEROMYCES MARXIANUS*

(75) Inventors: Rinji Akada, Yamaguchi (JP); Hisashi Hoshida, Yamaguchi (JP); Masamitsu Ide, Yamaguchi (JP)

(73) Assignee: Yamaguchi University, Yamaguchi (JP)

( * ) Notice: Subject to any disclaimer, the term of this patent is extended or adjusted under 35 U.S.C. 154(b) by 0 days.

(21) Appl. No.: 13/577,607

(22) PCT Filed: Feb. 7, 2011

(86) PCT No.: PCT/JP2011/000663
§ 371 (c)(1),
(2), (4) Date: Oct. 16, 2012

(87) PCT Pub. No.: WO2011/099263
PCT Pub. Date: Aug. 18, 2011

(65) Prior Publication Data
US 2013/0210107 A1   Aug. 15, 2013

(30) Foreign Application Priority Data
Feb. 9, 2010 (JP) ................................. 2010-026682

(51) Int. Cl.
C07H 21/04 (2006.01)
C12N 15/11 (2006.01)
C12N 15/81 (2006.01)
C12N 15/113 (2010.01)
C12N 9/12 (2006.01)
C12P 21/02 (2006.01)

(52) U.S. Cl.
CPC ............ *C12N 15/113* (2013.01); *C12N 15/815* (2013.01); *C12N 9/1205* (2013.01); *C12N 15/11* (2013.01); *C12P 21/02* (2013.01); *C12Y 207/01006* (2013.01); *C12N 15/81* (2013.01)

USPC .... 435/69.1; 435/71.1; 435/171; 435/254.11; 435/254.2; 435/254.21; 435/320.1; 536/24.1

(58) Field of Classification Search
None
See application file for complete search history.

(56) References Cited

U.S. PATENT DOCUMENTS 6,596,513 B2 * 7/2003 Williams et al. ............. 435/69.1
7,132,522 B1 * 11/2006 Becher et al. ................ 536/23.1

(Continued)

FOREIGN PATENT DOCUMENTS

EP  0 234 871  9/1987
JP  2007-089512  4/2007

(Continued)

OTHER PUBLICATIONS

International Preliminary Report on Patentability issued in International Application No. PCT/JP2011/000663 dated Oct. 4, 2012, with English Translation.

(Continued)

*Primary Examiner* — Rebecca Prouty
*Assistant Examiner* — Richard Ekstrom
(74) *Attorney, Agent, or Firm* — Venable LLP; Nancy J. Axelrod; Robert Kinberg

(57) ABSTRACT

Provided is a novel high-expression promoter, namely a GAL1 promoter, derived from *Kluyveromyces marxianus*. Also provided are the following, characterized by the use of the provided high-expression promoter; a recombinant polynucleotide containing said high-expression promoter; a vector containing said recombinant polynucleotide; a transformant obtained by introducing said recombinant polynucleotide or vector into yeast; a method using said transformant for high expression of a target gene; and a method using said transformant to manufacture the gene product of a target gene.

10 Claims, 2 Drawing Sheets

(56) References Cited

U.S. PATENT DOCUMENTS

| | | | |
|---|---|---|---|
| 7,943,366 B2* | 5/2011 | Rajgarhia et al. | 435/255.1 |
| 2004/0161841 A1* | 8/2004 | Dohner et al. | 435/252.3 |

FOREIGN PATENT DOCUMENTS

| | | |
|---|---|---|
| JP | 2008-029239 | 2/2008 |
| JP | 2008-237024 | 10/2008 |

OTHER PUBLICATIONS

International Search Report of PCT/JP2011/000663 Dated Mar. 8, 2011 With an English Translation.

Savitree Limtong et al., "Production of Fuel Ethanol At High Temperature From Sugar Cane Juice by a Newly Isolated Kluyveromyces Marxianus," Bioresource Technology 98, 3367-3374, 2007.

Gustavo Graciano Fonseca, et al., "The Yeast Kluyveromyces Marxianus and Its Biotechnological Potential," Appl. Microbiolo Biotechnol 79:339-354, 2008.

Sanom Nonklang et al., "High-Temperature Ethanol Fermentation and Transformation With Linear DNA in the Thermotolerant Yeast Kluyveromyces marxianus DMKU3-1042," Applied and Environmental Microbiology 74(24), P. 7514-7521, 2008.

M.A. Babiker et al., "High-Temperature Fermentation: How Can Processes for Ethanol Production At High Temperatures Become Superior to the Traditional Process Using Mesophilic Yeast?" Appl Microbiol Biotechnol, 85:861-867, 2010.

DNA Data Bank of Japan. [Online]., 2005, [Retrieved on Feb. 25, 2011]. Retrieved From the Internet: <http://getentry.ddbj.nig.ac.jp/>, Accession No. AL424781.

DNA Data Bank of Japan. [Online]., 2005, [Retrieved on Feb. 25, 2011]. Retrieved From the Internet: <http://getentry.ddbj.nig.ac.jp/>, Accession No. AL422787.

DNA Data Bank of Japan. [Online]., 2005, [Retrieved on Feb. 25, 2011]. Retrieved From the Internet: <http://getentry.ddbj.nig.ac.jp/>, Accession No. AL424207.

DNA Data Bank of Japan. [Online]., 2005, [Retrieved on Feb. 25, 2011]. Retrieved From the Internet: <http://getentry.ddbj.nig.ac.jp/>, Accession No. AL424782.

DNA Data Bank of Japan. [Online]., 2005, [Retrieved on Feb. 25, 2011]. Retrieved From the Internet: <http://getentry.ddbj.nig.ac.jp/>, Accession No. AL424206.

Sun Mee Park, et al., Galactose-Inducible Expression Systems in Candida maltosa Using Promoters of Newly-Isolated GAL1 and GAL10 Genes., Yeast., vol. 13, p. 21-29, 1997.

Brian L. Wickes et al., The Cryptococcus neoformans GAL7 Gene and Its Use As an Inducible Promoter, Mol. Microbiol., 16:6, p. 1099-1109, 1995.

Thomas D. Webster et al., Nucleotide Sequence of the Galactose Gene Cluster of Kluyveromyces Lactis., Nucleic Acids Res., 16:16, p. 8192-8194, 1988.

Jean-Luc Souciet et al., Genomic Exploration of the Hemiascomycetous Yeasts: 1. A Set of Yeast Species for Molecular Evolution Studies., FEBS Lett., vol. 487, p. 3-12, 2000.

Bertrand Llorente et al., Genomic Exploration of the Hemiascomycetous Yeasts: 12. Kluyveromyces marxianus Var. Marxianus., FEBS Lett., vol. 487, p. 71-75, 2000.

Extended European Search Report dated Aug. 14, 2013, issued in European Application No. 11742013.3.

Maya et al. "Systems for Applied Gene Control in Saccharomyces cerevisiae", Biotechnology Letters, vol. 30, Issue 6, pp. 979-987 (2008).

Almeida et al., Acquisition of Flocculation Phenotype by Kluyveromyces marxianus When Overexpressing Gap1 Gene Encoding an Isoform of Glyceraldehyde-3-Phosphate Dehydrogenase, Journal of Microbiological Methods, vol. 55, pp. 433-440 (2003).

Texeira, "A Comparative Analysis of the GAL Genetic Switch Between Not-So-Distant Cousins: Saccharomyces cerevisiae Versus Kluyveromyces lactis", Fems Yeast Research, vol. 5, pp. 1115-1128 (2005).

Pecota et al., "Evaluation of the Tetracycline Promoter System for Regulated Gene Expression in Kluyveromyces marxianus", Biotechnology and Bioengineering, vol. 92, issue 1, pp. 117-123 (2005).

* cited by examiner

Structure of KmGAL1 promoter

HIGH-EXPRESSION PROMOTER DERIVED FROM *KLUYVEROMYCES MARXIANUS*

CROSS-REFERENCE TO RELATED APPLICATIONS

This application is a U.S. National Stage of International Application No. PCT/JP2011/000663, filed Feb. 7, 2011, claiming priority to Japanese Application No. 2010-026682, filed Feb. 9, 2010.

SEQUENCE LISTING

The instant application contains a Sequence Listing which has been submitted in ASCII format via EFS-Web and is hereby incorporated by reference in its entirety. Said ASCII copy, created on Aug. 3, 2012, is named Sequence Listing.txt and is 7 KB in size.

TECHNICAL FIELD

The present invention relates to a novel high-expression promoter derived from *Kluyveromyces marxianus*, a recombinant polynucleotide containing the promoter, a vector containing the recombinant polynucleotide, a transformant obtained by introducing the recombinant polynucleotide or the vector into yeast, a method for highly expressing a target gene using the transformant and a method for producing a target gene product using the transformant.

BACKGROUND ART

Recently, with a progress of gene recombination technology, a wide variety of useful proteins have been successfully produced by use of a microorganism such as *Escherichia coli*. However, in the case where a foreign-protein gene derived from a eukaryote is expressed in *Escherichia coli* as a host, it is known that normal posttranslational modification such as normal processing and addition of a sugar chain is not made. This is a problem. For this reason, yeast, which is a eukaryote, is relatively frequently used as a host. As the host yeast, for example, *Saccharomyces cerevisiae*, *Pichia pastoris*, *Pichia methanolica*, *Schizosaccharomyces pombe*, *Hansenula anomala* and *Kluyveromyces lactis* are known (see, for example, patent document 1). However, the expression level of a foreign protein in a yeast used as a host could have been room for improvement.

To express a foreign-protein gene in a host, a recombinant polynucleotide, in which the foreign-protein gene has been placed operably under the control of a promoter capable of functioning in a host, is introduced into the host. In the resultant transformant, the foreign protein is expressed. Since the transcriptional activity of a promoter significantly influences the expression efficiency of the foreign protein, a promoter having a high transcriptional activity is generally used. Furthermore, it is preferable to induce expression of a foreign-protein gene with desired timing. This is because the efficiency for producing a foreign protein increases in fermentative production using a transformant, when the transformant is first allowed to proliferate as much as possible and then a foreign protein is expressed. As an inducible promoter having a high transcriptional activity, a galactose inducible promoter is well known. The galactose inducible promoter refers to a promoter which can be induced by galactose during glucose deficiency time. In *Saccharomyces cerevisiae*, etc., a promoter (GAL promoter) of a galactose metabolism gene (GAL gene) such as GAL1 promoter, GAL2 promoter, GAL3 promoter, GAL5 promoter, GAL7 promoter and GAL10 promoter, are frequently used (see for example, patent document 2).

In the meantime, *Kluyveromyces marxianus* is a heat resistant yeast (see for example, non-patent documents 1 and 2). In the case where ethanol fermentation is performed in yeasts generally employed, since fermentation heat raises the temperature of a fermentation liquor, cooling of the fermentation liquor was required in order to continuously perform ethanol fermentation. Therefore, to industrially perform ethanol fermentation, a large-scale cooling facility and tremendously large energy cost for cooling are indispensable. However, *Kluyveromyces marxianus*, which can proliferate at a temperature as high as 48° C. (non-patent documents 3 and 4), enables efficient ethanol fermentation without requiring such cooling facility and energy cost. The sequence of the GAL promoter of *Kluyveromyces marxianus* has not yet been elucidated.

PRIOR ART DOCUMENTS

Patent Documents

Patent Document 1: Japanese Unexamined Patent Application Publication No. 2008-29239
Patent Document 2: Japanese Unexamined Patent Application Publication No. 2007-89512

Non-patent Documents

Non-patent Document 1: Bioresource Technology (2007) 98, 3367-3374
Non-patent Document 2: Appl. Microbiol. Biotechnol. (2008) 79, 339-354
Non-patent Document 3: Applied and Environmental Microbiology (2008) 74, 7514-7521
Non-patent Document 4: Appl. Microbiol. Biotechnol. (2010) 85, 861-867

SUMMARY OF THE INVENTION

Object to be Solved by the Invention

An object of the present invention is to provide GAL1 promoter, which is a novel high-expression promoter derived from *Kluyveromyces marxianus*, a recombinant polynucleotide containing the high-expression promoter, a vector containing the recombinant polynucleotide, a transformant obtained by introducing the recombinant polynucleotide or the vector into yeast, a method for highly expressing a target gene using the transformant and a method for producing a target gene product using the transformant.

Means to Solve the Object

The present inventors conducted intensive studies. As a result, they have successfully isolated GAL1 promoter from *Kluyveromyces marxianus*, and found that the promoter can significantly highly express a target gene in *Kluyveromyces marxianus*, and also can highly express a target gene in *Saccharomyces cerevisiae*. Based on the findings, the present invention has been accomplished.

More specifically, the present invention relates to (1) a high-expression promoter consisting of any one of polynucleotides:
(a) the polynucleotide represented by SEQ ID NO: 1;
(b) a polynucleotide having an identity of 80% or more to the polynucleotide (a) and having a promoter activity in *Kluyveromyces marxianus* and at least one or more yeasts other than *Kluyveromyces marxianus*;

(c) the polynucleotide represented by SEQ ID NO: 2;

(d) a polynucleotide having an identity of 80% or more to the polynucleotide (c) and having a promoter activity in *Kluyveromyces marxianus* and at least one or more yeasts other than *Kluyveromyces marxianus*;

(e) the polynucleotide represented by SEQ ID NO: 3; and (f) a polynucleotide having an identity of 80% or more to the polynucleotide (e) and having a promoter activity in *Kluyveromyces marxianus* and at least one or more yeasts other than *Kluyveromyces marxianus*.

Furthermore, the present invention relates to (2) a recombinant polynucleotide containing the high-expression promoter according to (1) and a target gene operably placed under the control of the promoter.

Furthermore, the present invention relates to (3) a vector containing the recombinant polynucleotide according to (2).

Furthermore, the present invention relates to (4) a transformant obtained by introducing the recombinant polynucleotide according to (2) or the vector according to (3) into a yeast; (5) the transformant according to (4) wherein the yeast is any one selected from the group consisting of yeasts belonging to the genus *Saccharomyces* and the genus *Kluyveromyces*; and (6) the transformant according to (4) wherein the yeast is any one selected from *Saccharomyces cerevisiae* and *Kluyveromyces marxianus*.

Furthermore, the present invention relates to (7) a method for highly expressing a target gene, comprising a step of culturing the transformant according to any one of (4) to (6).

Furthermore, the present invention relates to (8) a method for producing a target gene product, comprising a step of culturing the transformant according to any one of (4) to (6) and a step of recovering a target gene product from the transformant obtained by the culturing.

Effect of the Invention

The high-expression promoter of the present invention can highly express a target gene not only in *Kluyveromyces marxianus* but also in other yeasts. For example, if the high-expression promoter of the present invention is used in *Saccharomyces cerevisiae*, a target gene can be expressed at a higher level than that expressed by GAL10 promoter of *Saccharomyces cerevisiae*. Accordingly, if the high-expression promoter of the present invention is used, a target gene product can be also produced efficiently.

MODE OF CARRYING OUT THE INVENTION

1. Promoter of the Present Invention

Figure 1:
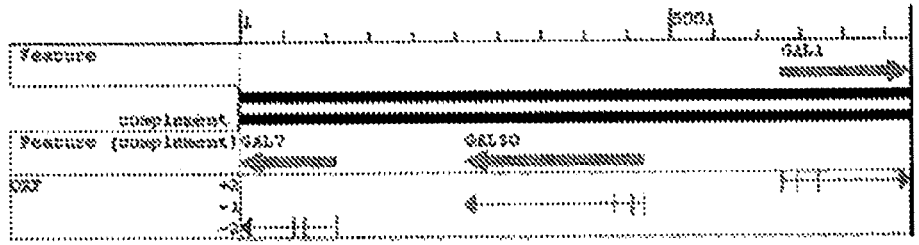
FIG. 1 This is an illustration showing the structures of GAL1 promoter, GAL10 promoter and GAL7 promoter in *Kluyveromyces marxianus*.

The high-expression promoter of the present invention is characterized by consisting of (A) a polynucleotide represented by SEQ ID NO: 1, 2 or 3 or (B) a polynucleotide which is a mutant of any one of these polynucleotides, and has a promoter activity in *Kluyveromyces marxianus* and at least one or more yeasts other than *Kluyveromyces marxianus*. The polynucleotide represented by SEQ ID NO: 1 is GAL1 promoter derived from *Kluyveromyces marxianus*; the polynucleotide represented by SEQ ID NO: 2 is GAL10 promoter derived from *Kluyveromyces marxianus*; and the polynucleotide represented by SEQ ID NO: 3 is GAL7 promoter derived from *Kluyveromyces marxianus*. The high-expression promoter of the present invention can highly express a target gene not only in *Kluyveromyces marxianus* but also in other yeasts.

The promoter (hereinafter specifically referred to also as a "mutant promoter of the present invention") consisting of the polynucleotide (B) which is a mutant of the polynucleotide represented by SEQ ID NO: 1, 2 or 3, and has a promoter activity in *Kluyveromyces marxianus* and at least one or more yeasts other than *Kluyveromyces marxianus*, includes:

(a) a polynucleotide having an identity of 80% or more, preferably 85% or more, more preferably 90% or more, further preferably 95% or more, and most preferably 98% or more to the polynucleotide represented by SEQ ID NO: 1, 2 or 3 and having a promoter activity in *Kluyveromyces marxianus* and at least one or more yeasts other than *Kluyveromyces marxianus*;

(b) a polynucleotide having a deletion, substitution or addition of one or more nucleotides in the polynucleotide represented by SEQ ID NO: 1, 2 or 3 and having a promoter activity in *Kluyveromyces marxianus* and at least one or more yeasts other than *Kluyveromyces marxianus*; and (c) a polynucleotide hybridizing with a polynucleotide complementary to the polynucleotide represented by SEQ ID NO: 1, 2 or 3 under stringent conditions and having a promoter activity in *Kluyveromyces marxianus* and at least one or more yeasts other than *Kluyveromyces marxianus*.

The "a polynucleotide having a deletion, substitution or addition of one or more nucleotides" in item (b) refers to a polynucleotide having a deletion, substitution or addition of an arbitrary number of nucleotides, for example, 1 to 20, preferably 1 to 15, more preferably 1 to 10 and further preferably 1 to 5.

The "under stringent conditions" in item (c) refers to the conditions in which a so-called specific hybrid is formed and a nonspecific hybrid is not formed, and specifically, can include the conditions in which DNAs having an identity of 80% or more and preferably 85% or more are mutually hybridized and DNAs having an identity lower than the above percentage are not hybridized or the conditions used for washing of general Southern hybridization, that is, 65° C., 1×SSC solution (the composition of 1×SSC solution: 150 mM sodium chloride, 15 mM sodium citrate), 0.1% SDS, or a salt concentration corresponding to 0.1×SSC, 0.1% SDS, in which hybridization is made. Hybridization can be performed in accordance with the method described in e.g., Molecular Cloning, the 2nd edition. As an example of the "polynucleotide hybridized under stringent conditions" in item (c), a polynucleotide having at least a predetermined identity to a polynucleotide, which is complementary to a polynucleotide used as a probe, can be mentioned. For example, a polynucleotide having an identity of 80% or more, preferably 85% or more, more preferably 90% or more, further preferably 95% or more, most preferably 98% or more is preferably mentioned.

Note that, positions 758 to 774, positions 779 to 795, positions 804 to 820, positions 825 to 841, and positions 860 to 876 of the polynucleotide represented by SEQ ID NO: 1;

positions 718 to 734, positions 753 to 769, positions 774 to 790, positions 799 to 815, and positions 820 to 836 of the polynucleotide represented by SEQ ID NO: 2; and positions 939 to 955, positions 954 to 970, and positions 988 to 1004 of the polynucleotide represented by SEQ ID NO: 3 are each a binding site for a transcription factor, GAL4.

The polynucleotide represented by SEQ ID NO: 1, 2 or 3 of item (A), since its nucleotide sequence has been elucidated, can be obtained, for example, by PCR using genomic DNA of *Kluyveromyces marxianus* as a template and an oligonucleotide synthesized based on the nucleotide sequence, as a primer or also by hybridization using the oligonucleotide synthesized based on the nucleotide sequence, as a probe. Note that chromosomal DNA can be obtained by a method disclosed in the conventional method (for example, Japanese Unexamined Patent Application Publication No. 2008-237024).

An oligonucleotide can be synthesized, for example, by using commercially available various DNA synthesis apparatuses in accordance with a conventional method. Furthermore, PCR can be performed by thermal cycler GeneAmp PCR System 2400 manufactured by Applied Biosystems using e.g., Taq DNA polymerase (manufactured by Takara Bio Inc.) and KOD-Plus—(manufactured by Toyobo Co., Ltd.) in accordance with a conventional method.

Furthermore, a polynucleotide mutant in the aforementioned mutant promoter of the present invention can be also prepared in any known method to those skilled in the art, such as chemical synthesis, genetic engineering procedure or mutagenesis. Specifically, a polynucleotide mutant can be obtained by subjecting the polynucleotide represented by SEQ ID NO: 1, 2 or 3 to a method of bringing into contact with an agent serving as a mutagen, a method of irradiating with UV rays or a genetic engineering procedure, etc, thereby introducing a mutation into any one of these polynucleotides. One of the genetic engineering procedures, i.e., a site specific mutagenesis, is useful since it is a procedure capable of introducing a specific mutation into a specific position and carried out in accordance with the method described in e.g., Molecular Cloning, the second edition, and Current Protocols in Molecular Biology, Supplement 1 to 38, John Wiley & Sons (1987-1997).

The high-expression promoter of the present invention has a promoter activity in *Kluyveromyces marxianus* and at least one or more yeasts other than *Kluyveromyces marxianus*. Whether a polynucleotide has a promoter activity in a certain yeast can be easily determined by e.g., a well known reporter assay, which includes, for example, a step of preparing a recombinant polynucleotide, in which a reporter gene is linked operably downstream of the polynucleotide, a step of obtaining a transformed yeast by transforming the yeast with the recombinant polynucleotide, and a step of measuring the degree of expression of the reporter gene in the transformed yeast.

Examples of the "yeast other than *Kluyveromyces marxianus*" in the "*Kluyveromyces marxianus* and at least one or more yeasts other than *Kluyveromyces marxianus*" is not particularly limited as long as it is a yeast other than *Kluyveromyces marxianus*. Preferable examples thereof include yeasts belonging to the genus *Kluyveromyces* other than *Kluyveromyces marxianus*, such as *Kluyveromyces lactis*; yeasts belonging to the genus *Saccharomyces*, such as *Saccharomyces cerevisiae*; yeasts belonging to the genus *Candida*, such as *Candida albicans*; yeasts belonging to the genus *Zygosaccharomyces* such as *Zygosaccharomyces rouxii*; yeasts belonging to the genus *Schizosaccharomyces*, such as *Schizosaccharomyces pombe*; and yeasts belonging to the genus *Pichia*, such as *Pichia pastoris*. Of them, yeasts belonging to the genus *Kluyveromyces* other than *Kluyveromyces marxianus*, such as *Kluyveromyces lactis* and yeasts belonging to the genus *Saccharomyces* such as *Saccharomyces cerevisiae* can be more preferably mentioned as examples. Of them, yeasts belonging to the genus *Saccharomyces* such as *Saccharomyces cerevisiae* can be further preferably mentioned as examples and *Saccharomyces cerevisiae* can be particularly preferably mentioned as an example.

The "high expression" in the high-expression promoter of the present invention and the method for highly expressing a target gene of the present invention described later and the "high efficiency" in the method for producing a target gene product of the present invention described later, preferably include in the case of (X) where a host is *Kluyveromyces marxianus*, when a transformant obtained by introducing a recombinant polynucleotide, in which a secretory luciferase CLuc gene is linked operably downstream of the promoter, into *Kluyveromyces marxianus*, is cultured with shaking in an YPGal liquid medium (1 mass % yeast extract, 2 mass % polypeptone, 2 mass % galactose) at 28° C. for 48 hours, the relative expression level (RLU/OD·µl) of the secretory luciferase CLuc in the culture solution being 25000 or more, preferably 28000 or more, more preferably 32000 or more, and further preferably 34000 or more; and in the case of (Y) where a host is a yeast other than *Kluyveromyces marxianus* (preferably *Saccharomyces cerevisiae*), when a transformant obtained by introducing a recombinant polynucleotide, in which a secretory luciferase CLuc gene is linked operably downstream of the promoter, into the yeast, is cultured with shaking in an YPGal liquid medium (1 mass % yeast extract, 2 mass % polypeptone, 2 mass % galactose) at 28° C. for 48 hours, the relative expression level (RLU/OD·µl) of the secretory luciferase CLuc in the culture solution being 1500 or more, preferably 2000 or more, more preferably 2500 or more, and further preferably 3000 or more. Furthermore, it is more preferable to satisfy (X) and (Y).

Another example of the "high expression" in the high-expression promoter of the present invention and the method for highly expressing a target gene of the present invention described later and "high efficiency" in the method for producing a target gene product of the present invention described later, preferably include a ratio of the relative expression level (RLU/OD·µl) of secretory luciferase CLuc in the culture solution, when a transformant obtained by introducing a recombinant polynucleotide, in which a secretory luciferase CLuc gene is linked operably downstream of the promoter, into *Kluyveromyces marxianus*, is cultured with shaking in an YPGal liquid medium (1 mass % yeast extract, 2 mass % polypeptone, 2 mass % galactose) at 28° C. for 48 hours, relative to the relative expression level (RLU/OD·µl) of secretory luciferase CLuc in the culture solution, when a transformant obtained by introducing a recombinant polynucleotide, in which a secretory luciferase CLuc gene is linked operably downstream of the GAL10 promoter of *Saccharomyces cerevisiae*, into *Saccharomyces cerevisiae*, is cultured with shaking in an YPGal liquid medium (1 mass % yeast extract, 2 mass % polypeptone, 2 mass % galactose) at 28° C. for 48 hours, being 10 times or more, preferably 20 times or more, more preferably 30 times or more, further preferably 40 times or more, and most preferably 50 times or more.

A still another example of the "high expression" in the high-expression promoter of the present invention and the method for highly expressing a target gene of the present invention described later and "high efficiency" in the method for producing a target gene product of the present invention described later, preferably includes a ratio of the relative expression level (RLU/OD·μl) of secretory luciferase CLuc in the culture solution, when a transformant obtained by introducing a recombinant polynucleotide, in which a secretory luciferase CLuc gene is linked operably downstream of the promoter, into *Kluyveromyces marxianus*, is cultured with shaking in an YPGal liquid medium (1 mass % yeast extract, 2 mass % polypeptone, 2 mass % galactose) at 28° C. for 48 hours, relative to the relative expression level (RLU/OD·μl) of secretory luciferase CLuc in the culture solution, when a transformant obtained by introducing the recombinant polynucleotide into *Saccharomyces cerevisiae* is cultured with shaking in an YPGal liquid medium (1 mass % yeast extract, 2 mass % polypeptone, 2 mass % galactose) at 28° C. for 48 hours, being twice or more, preferably 3 times or more, further preferably 4 times or more, and most preferably 5 times or more.

As the polynucleotide in the present invention, a complementary double stranded polynucleotide is preferably mentioned as an example. Of them, a complementary double stranded DNA is particularly preferably mentioned as an example.

2. Recombinant Polynucleotide of the Present Invention.

The recombinant polynucleotide of the present invention is characterized by containing the high-expression promoter of the present invention and a target gene placed operably under the control of the promoter. The recombinant polynucleotide of the present invention can highly express a target gene product (protein and peptide) encoded by the target gene in a galactose-inducible manner through activation of the high-expression promoter of the present invention.

In the present invention, the "target gene placed operably under the control of the high-expression promoter of the present invention" means that the high-expression promoter of the present invention is linked to the target gene such that expression of the target gene is induced by binding a transcription factor to the high-expression promoter of the present invention. As the "target gene", any gene may be used and preferably a useful protein gene encoding any useful protein can be preferably mentioned as an example. As the useful-protein gene, a cellulase gene, a carbohydrase gene such as an amylase gene and a gene of a viral vaccine protein can be preferably mentioned as examples.

3. Vector Containing the Recombinant Polynucleotide of the Present Invention

A vector containing the recombinant polynucleotide of the present invention is characterized by containing the recombinant polynucleotide of the present invention described above. The vector of the present invention can hold the recombinant polynucleotide of the present invention in a host yeast, and can transform the yeast in order to express a target gene. The vector in the present invention may be linear or cyclic. In the case where the host yeast is *Kluyveromyces marxianus*, even if the vector is linear, recombination can highly frequently take place on the chromosome, with the result that transformation occurs. Furthermore, in the case of a cyclic vector, if the vector contains a self-replication sequence, the vector can be autonomously replicated within a yeast cell and held in the yeast cell, with the result that transformation occurs.

The vector is not particularly limited as long as it can express a target gene in a yeast cell. As the cyclic plasmid vector, for example, pKD1 can be preferably mentioned.

4. Transformant of the Present Invention

The transformant of the present invention is characterized by being obtained by introducing the recombinant polynucleotide of the present invention or the vector of the present invention into a yeast. The transformant of the present invention can highly express a target gene in the cell in a galactose-inducible manner. The target gene product can be efficiently produced by culturing the transformant of the present invention.

The type of yeast used in preparing the transformant of the present invention is not particularly limited. Preferable examples thereof include yeasts belonging to the genus *Kluyveromyces* such as *Kluyveromyces marxianus* and *Kluyveromyces lactis*; yeasts belonging to the genus *Saccharomyces* such as *Saccharomyces cerevisiae*; yeasts belonging to the genus *Candida* such as *Candida albicans*; yeasts belonging to the genus *Zygosaccharomyces* such as *Zygosaccharomyces rouxii*; yeasts belonging to the genus *Schizosaccharomyces* such as *Schizosaccharomyces pombe*; and yeasts belonging to the genus *Pichia* such as *Pichia pastoris*. Of them, yeasts belonging to the genus *Kluyveromyces* such as *Kluyveromyces marxianus* and *Kluyveromyces lactis*; and yeasts belonging to the genus *Saccharomyces* such as *Saccharomyces cerevisiae* are more preferably mentioned as examples. Of them, in view of high expression level of a target gene and high production efficiency of a target gene product, *Kluyveromyces marxianus* can be particularly preferably mentioned as an example. Furthermore, *Kluyveromyces marxianus* is preferable because it has heat resistance and thus ethanol fermentation can be efficiently made without requiring a facility for cooling fermentation heat and energy cost.

A method for introducing the recombinant polynucleotide of the present invention or the vector of the present invention into a yeast is not particularly limited. Examples thereof include known methods including biological methods such as a method of using a viral vector, a method of using a specific receptor and a cell fusion method; physical methods such as an electroporation method, a microinjection method, a gene gun method and an ultrasound mediated gene transfer method; and chemical methods such as a lipofection method, a calcium phosphate coprecipitation method, a liposome method and a DEAE dextran method. Of them, a lipofection method can be preferably mentioned as an example since it is easy and commonly used. Furthermore, whether the recombinant polynucleotide of the present invention or the vector of the present invention is introduced into the yeast can be easily determined, for example, by inserting a marker gene to the recombinant polynucleotide of the present invention and the vector of the present invention as a target gene or in addition to the target gene, and then checking the expression of the marker gene in a transformant.

5. Method for Highly Expressing a Target Gene of the Present Invention

A method for highly expressing a target gene of the present invention is characterized by including a step of culturing the transformant of the present invention. As the "method for culturing the transformant of the present invention" is not particularly limited as long as the transformant can be amplified. For example, a method for culturing the transformant under temperature conditions (for example, 25 to 33° C., preferably 28 to 30° C.) in which the transformant can be amplified, in YPD medium (1 mass % yeast extract, 2 mass % polypeptone, 2 mass % glucose) for an appropriate time (for example, 1 to 10 days, preferably 1 to 5 days, more preferably 1 to 3 days) with shaking is preferably mentioned.

6. Method for Producing a Target Gene Product of the Present Invention

A method for producing a target gene product of the present invention is characterized by including a step of culturing the transformant of the present invention and a step of recovering a target gene product from the transformant obtained by culturing. According to the production method, a target gene product can be highly efficiently produced. The method for "recovering a target gene product from the transformant obtained by culturing" is not particularly limited as long as a target gene product can be recovered. A known method such as a method of using chromatography and a method of using a tag can be mentioned as examples.

EXAMPLES

Example 1

Isolation of KmGAL1 Promoter from *Kluyveromyces marxianus*

The present inventors obtained a draft genome sequence for the genome sequence of *Kluyveromyces marxianus* DMKU3-1042 strain by Genome Sequencer FLX System (Roche Diagnostics K.K.). However, in a first sequencing, only a partial sequence of GAL was obtained. Then, further high performance Genome Sequencer FLX Titanium (Roche Diagnostics K.K.) was used. Owing to this, at last, a draft genome sequence was successfully obtained. To obtain a galactose inducible promoter from *Kluyveromyces marxianus*, the present inventors searched a draft genome sequence of *Kluyveromyces marxianus* based on the sequence information of known GAL1, GAL10 and GAL7 derived from *Saccharomyces cerevisiae*. As a result, they found a sequence having relatively high identity to the GAL promoter derived from *Saccharomyces cerevisiae* in the draft genome sequence of *Kluyveromyces marxianus* and isolated the sequence. The structure of the promoter of the isolated sequence is shown in FIG. 1. As shown in FIG. 1, GAL10 promoter and GAL7 promoter are placed in a reverse direction of GAL1 promoter. A GAL4 binding site was found between GAL1 promoter and GAL10 promoter. Note that, the arrangement of these GAL1 promoter (KmGAL1 promoter), GAL10 promoter (KmGAL10 promoter) and GAL7 promoter (KmGAL1 promoter) in *Kluyveromyces marxianus* was the same as that of these promoters in *Saccharomyces cerevisiae* which had been already elucidated. Note that, the experiments performed by using a GAL1-like promoter in the sequence isolated this time in Example 2 and Example 3 described later demonstrated that the GAL promoters derived from *Kluyveromyces marxianus* and isolated this time are each GAL promoter.

Example 2

Identification of a KmGAL1 Promoter Site

To identify a KmGAL1 promoter site, the following expression analysis test was performed.

Figure 2:
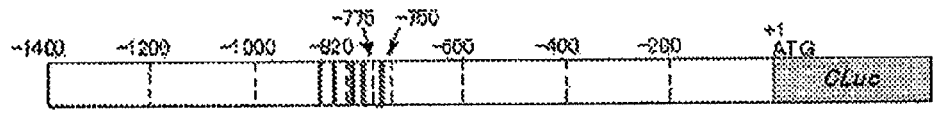
FIG. 2 This is an illustration showing the structure of GAL1 promoter (KmGAL1 promoter) of *Kluyveromyces marxianus*.

First, a 1.4 kb DNA sequence (sequence corresponding to −1400 to −1 of KmGAL1 promoter structure shown in FIG. 2), which conceivably contained KmGAL1 promoter, was prepared and designated as KmGAL1-1400. Next, a DNA sequence (sequence corresponding to −1200 to −1 of KmGAL1 promoter structure shown in FIG. 2) was prepared by deleting 200 bases from the 5' end of KmGAL1-1400 and designated as KmGAL1-1200. Similarly, a DNA sequence (sequence corresponding to −1000 to −1 of KmGAL1 promoter structure shown in FIG. 2) was prepared by deleting 400 bases from the 5' end of KmGAL1-1400 and designated as KmGAL1-1000. Similarly, a DNA sequence (sequence corresponding to −820 to −1 of KmGAL1 promoter structure shown in FIG. 2) was prepared by deleting 580 bases from the 5' end of KmGAL1-1400 and designated as KmGAL1-820. Similarly, a DNA sequence (sequence corresponding to −775 to −1 of KmGAL1 promoter structure shown in FIG. 2) was prepared by deleting 625 bases from the 5' end of KmGAL1-1400 and designated as KmGAL1-775. Similarly, a DNA sequence (sequence corresponding to −750 to −1 of KmGAL1 promoter structure shown in FIG. 2) was prepared by deleting 650 bases from the 5' end of KmGAL1-1400 and designated as KmGAL1-750. Similarly, a DNA sequence (sequence corresponding to −600 to −1 of KmGAL1 promoter structure shown in FIG. 2) was prepared by deleting 800 bases from the 5' end of KmGAL1-1400 and designated as KmGAL1-600. Similarly, a DNA sequence (sequence corresponding to −400 to −1 of KmGAL1 promoter structure shown in FIG. 2) was prepared by deleting 1000 bases from the 5' end of KmGAL1-1400 and designated as KmGAL1-400. Similarly, a DNA sequence (sequence corresponding to −200 to −1 of KmGAL1 promoter structure shown in FIG. 2) was prepared by deleting 1200 bases from the 5' end of KmGAL1-1400 and designated as KmGAL1-200.

Figure 3:
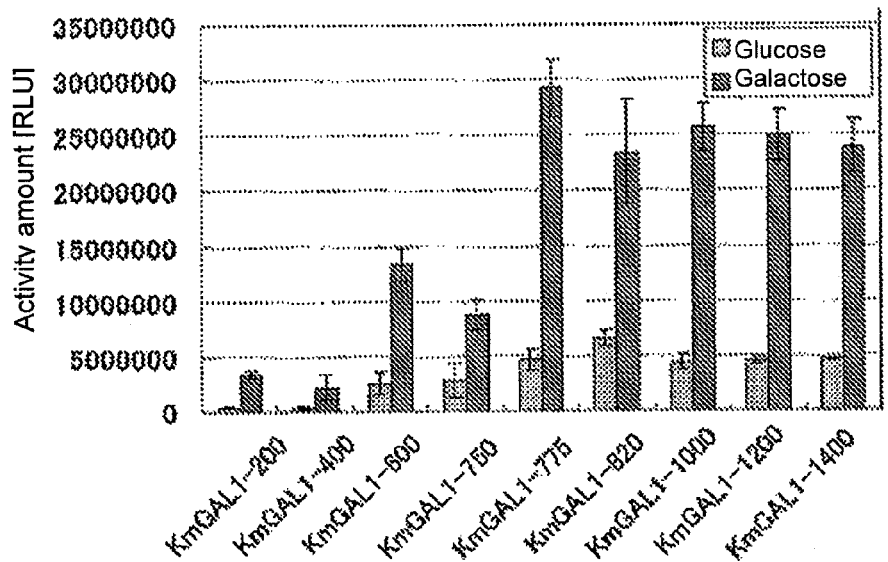
FIG. 3 This is a bar chart showing the results of an expression analysis test for identifying the site of KmGAL1 promoter.

Using a template in which a secretory luciferase CLuc gene was linked downstream of a GAL1 promoter and the 9 types of DNA sequences such as KmGAL1-1400 mentioned above, PCR synthesis was performed. By this, 9 types of recombinant DNAs such as KmGAL1-1400-CLuc having the secretory luciferase CLuc gene operably linked downstream of each of the 9 types of DNA sequences such as KmGAL1-1400 mentioned above were obtained. The obtained 9 types of recombinant DNAs were separately introduced into *Kluyveromyces marxianus* to obtain 9 types of transformants in total. The 9 types of transformants (2 clones per type) were cultured with shaking in YPD liquid medium (1 mass % yeast extract, 2 mass % polypeptone, 2 mass % glucose) at 28° C., for 48 hours. A culture solution (5 μl) of each type of transformants was taken as a sample to determine the relative expression level (RLU: Relative Luciferase Unit) of secretory luciferase CLuc. Furthermore, the same shaking culture was performed by using YPGal liquid medium (1 mass % yeast extract, 2 mass % polypeptone, 2 mass % galactose) in place of the YPD liquid medium to determine the relative expression level of secretory luciferase CLuc. These results are shown in FIG. 3. Note that, in the bar chart, two bars are drawn at the name of every promoter (e.g., KmGAL1-1400): the left bar represents an average value of two clones grown in YPD liquid medium (glucose medium); whereas the right bar represents an average value of two clones grown in YPGal liquid medium (galactose medium). As is apparent from the results of FIG. 3, when KmGAL1-1400, KmGAL1-1200, KmGAL1-1000, KmGAL1-820 and KmGAL1-775 were used, both relative expression level of CLuc and the induction rate by galactose in the medium were extremely high. In contrast, when KmGAL1-750, KmGAL1-600, KmGAL1-400 and KmGAL1-200 were used, the relative expression level of CLuc was considerably low compared to the case where KmGAL1-1400, etc. was used. From the results, the portion corresponding to −775 to 750 of the KmGAL1 promoter structure shown in FIG. 2 was demonstrated to be particularly important for promoter activity. In this manner, the site of the KmGAL1 promoter was identified. Note that, the "activity amount" in the specification is synonymous with "relative expression level".

Example 3

Expression Analysis of KmGAL1 Promoter

To check how frequently a target gene can be expressed by KmGAL1 promoter in *Kluyveromyces marxianus* and how frequently a target gene can be expressed in yeasts other than *Kluyveromyces marxianus*, the following expression analysis test was performed.

First, PCR was performed by using URA3-5'40-KmGAL10c2 primer (SEQ ID NO: 4) and 15GKmGAL1+22c primer (SEQ ID NO: 5) and a chromosome genome derived from *Kluyveromyces marxianus* to obtain a sequence of KmGAL1 promoter (KmGAL1p).

Next, the following 4 transformants were prepared by a known transformation method.

Figure 4:
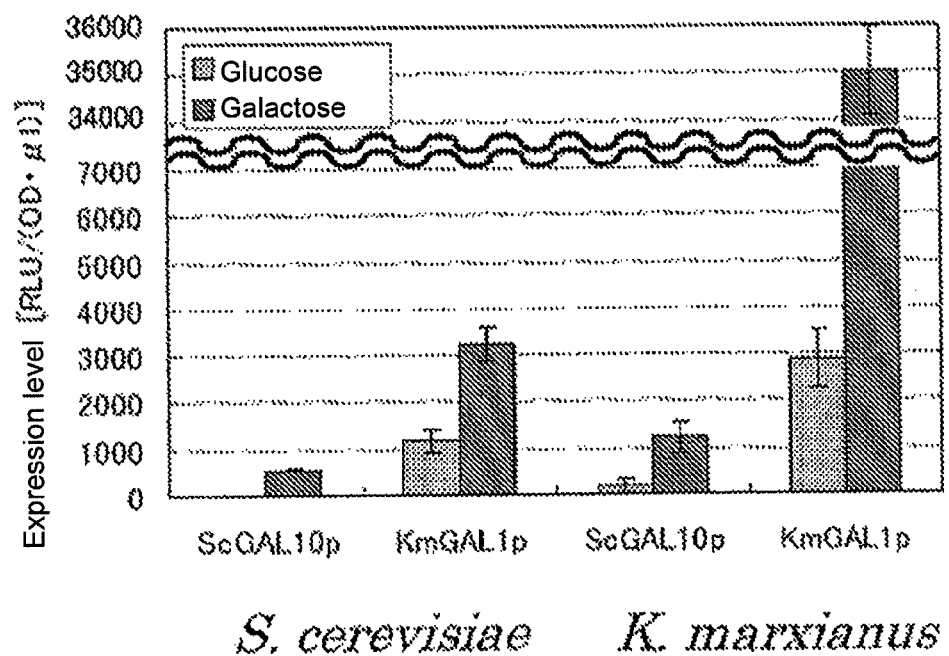
FIG. 4 This is a bar chart showing the results of an expression analysis test of KmGAL1 promoter in *Kluyveromyces marxianus* or *Saccharomyces cerevisiae*.

(1) A transformant obtained by introducing KmGAL1p-CLuc, in which a secretory luciferase CLuc gene was operably linked downstream of KmGAL1p, into *Kluyveromyces marxianus* (KmGAL1p at rightmost side of FIG. 4).

(2) A transformant obtained by introducing ScGAL10p-CLuc, in which a secretory luciferase CLuc gene was operably linked downstream of GAL10 promoter derived from *Saccharomyces cerevisiae*, into *Kluyveromyces marxianus* (ScGAL10p at the second right side of FIG. 4).

(3) A transformant obtained by introducing KmGAL1p-CLuc into *Saccharomyces cerevisiae* (KmGAL1p at the third right side of FIG. 4).

(4) A transformant obtained by introducing ScGAL10p-CLuc into *Saccharomyces cerevisiae* (ScGAL10p at the leftmost side of FIG. 4).

These transformants were separately cultured with shaking in YPD liquid medium (1 mass % yeast extract, 2 mass % polypeptone, 2 mass % glucose) at 28° C. for 48 hours. Thereafter, a culture solution (5 µl) of each type of transformants was taken as a sample to determine the relative expression level (RLU/OD·µl) of secretory luciferase CLuc. Furthermore, the same shaking culture was performed by using YPGal liquid medium (1 mass % yeast extract, 2 mass % polypeptone, 2 mass % galactose) in place of YPD liquid medium to determine the relative expression level of secretory luciferase CLuc. These results are shown in FIG. 4. Note that, in the bar chart, two bars are drawn at the name of every promoter (e.g., KmGAL1p): the left bar represents an average value of two clones grown in YPD liquid medium (glucose medium); whereas the right bar represents an average value of two clones grown in YPGal liquid medium (galactose medium).

As is apparent from the results of FIG. 4, KmGAL1 promoter performs expression also in *Saccharomyces cerevisiae* in a galactose-inducible manner. In addition, in the case where KmGAL1 promoter was used in *Saccharomyces cerevisiae*, the relative expression level (RLU/OD·µl) (under induction of galactose) of CLuc was about 5 times as high as that of the case where an ScGAL10 promoter was used, in terms of proportion. Generally, a promoter isolated from an organism belonging to a different type from that the host belongs to, does not function as a promoter in the host in most cases. In addition, it is usually impossible that a promoter of another type of organism attains an expression level beyond that attained by the promoter derived from a host. Therefore, it is an extremely rare phenomenon where GAL1 promoter derived from *Kluyveromyces marxianus* exhibits an expression level, in *Saccharomyces cerevisiae*, which is 5 times as high as that of GAL10 promoter derived from *Saccharomyces cerevisiae*.

Furthermore, in the case where KmGAL1 promoter was used in *Kluyveromyces marxianus*, the relative expression level (RLU/OD·µl) (under induction of galactose) of CLuc was 50 times or more as high as the relative expression level (under induction of galactose) of CLuc in the case where an ScGAL10 promoter was used in *Saccharomyces cerevisiae*, in terms of proportion. From this, it is said that the high expression performance that the KmGAL1 promoter has is significant.

INDUSTRIAL APPLICABILITY

The present invention can be particularly usefully used in the fields requiring high expression of a target gene and high yield of a target gene product.

The invention claimed is:

1. A recombinant polynucleotide comprising a promoter consisting of
the polynucleotide consisting of the nucleotide sequence of nucleotide numbers 816 to 1590 in SEQ ID NO: 1,
wherein when a transformant obtained by introducing a recombinant polynucleotide, in which a secretory luciferase CLuc gene is operably linked downstream of the promoter, into *Kluyveromyces marxianus*, is cultured with shaking in an YPGal liquid medium (1 mass % yeast extract, 2 mass % polypeptone, 2 mass % galactose) at 28° C. for 48 hours, the relative expression level (RLU/OD·μl) of the secretory luciferase CLuc in the culture solution is 25000 or more, and when a transformant obtained by introducing a recombinant polynucleotide, in which a secretory luciferase CLuc gene is operably linked downstream of the promoter, into *Saccharomyces cerevisiae*, is cultured with shaking in an YPGal liquid medium (1 mass % yeast extract, 2 mass % polypeptone, 2 mass % galactose) at 28° C. for 48 hours, the relative expression level (RLU/OD·μl) of the secretory luciferase CLuc in the culture solution is 1500 or more; and
a target gene other than the gene encoding GAL1 of *Kluyveromyces marxianus*, operably placed under control of the promoter.

2. A vector comprising the recombinant polynucleotide according to claim 1.

3. A transformant obtained by introducing the recombinant polynucleotide according to claim 1 into a yeast which is any one selected from the group consisting of yeasts belonging to the genus *Saccharomyces* and the genus *Kluyveromyces*.

4. The transformant according to claim 3, wherein the yeast is any one selected from the group consisting of *Saccharomyces cerevisiae* and *Kluyveromyces marxianus*.

5. A method for expressing a target gene, comprising a step of culturing the transformant according to claim 3 in a medium containing galactose.

6. A method for producing a target gene product, comprising a step of culturing the transformant according to claim 3 in a medium containing galactose and a step of recovering a target gene product from the transformant obtained by the culturing.

7. A transformant obtained by introducing the vector according to claim 2 into a yeast which is any one selected from the group consisting of yeasts belonging to the genus *Saccharomyces* and the genus *Kluyveromyces*.

8. The transformant according to claim 7, wherein the yeast is any one selected from the group consisting of *Saccharomyces cerevisiae* and *Kluyveromyces marxianus*.

9. A method for expressing a target gene, comprising a step of culturing the transformant according to claim 7 in a medium containing galactose.

10. A method for producing a target gene product, comprising a step of culturing the transformant according to claim 7 in a medium containing galactose and a step of recovering a target gene product from the transformant obtained by the culturing.

* * * * *

SEQUENCE LISTING

```
<160> NUMBER OF SEQ ID NOS: 5

<210> SEQ ID NO 1
<211> LENGTH: 1590
<212> TYPE: DNA
<213> ORGANISM: Kluyveromyces marxianus

<400> SEQUENCE: 1
catttcttga ttgttcttga tgttttttg gttttttcta gtttgcttgg aatcctatac      60
ttttagggtc tccagactat tactatttta ccttttggtt gttatagaca aacaaactaa    120
ccagacatat atacatatat atatatatat acactttcaa atggacatac acacgaataa    180
taataatagt aataacaaca ctctctccaa actgaaacac aacacactta tttatacaac    240
gtgcccgaat cgaaagtgtt tctgaagact tctaagaacc ggctgacaag attcaggcaa    300
ctccttatat actgtgtata tctgacactg caaaggcaga gcgagccaac tatcatatgc    360
ttagctgcct atacttcggg gcacacacat acacattgcc atatgccagc ttgcgtaagc    420
aaggaacgga tggagtgcca atcatccatc catcaatcac attcacaaca gaaaagcttg    480
ctaatgtgcc actactacta ctgttcttgc gcgtttcggc gcacagtgcc cagtggccag    540
gcgtaaagaa acgctggtac cacaccagca agcagcacca caggtgctgc tagaagcgaa    600
gcctggaatt gggatgcctt gagtgagaat acctggaaac ccggggcaga gagaggggg     660
```

```
gagaaacggt tccttgcgcg ggcttttctg ggtggtttag gtatgtgttt tggtttctt    720 gttttttggtt ttggttttgg ttttttggttt ggttttccgg aaggcagtgg gccgcgcgcg  780
gggtggagtg caccgggtgc gcacggacca tacctgtccg aacccgggga gtacgcggcc   840
gaatttgatc acgtgtacgc ggaacacagt gggccgtccc cgcatgccat tgttccagct   900
ggcgatcggc tggggttagt tagtacagtc tagtacagtc tagtaccggc ttgctactgc   960
tttcctacgc cgcgccgcgc cgccacatcc tggaataatc ccatcccatc ccaccttgta  1020
tatcgcggcg agcggtggtg gtgctcatga gattattttt attatactta ctttacgtta  1080
ccttagtgtt tttttgttt tttttttct cttctgtag ctcccttct actatgcggc     1140 atgcgctctg tgccgtgctg taatgtaagt tttgtgatta ttgactgatt ctttggaggg  1200
ccccactgtt ttttaatttg ttcttttttt cgtcatatca cttttaaag gtacaaggtt   1260 tctttgtaaa atgggcagcg caaaagatat aaaagacatg ggtgtttgag cattgggaca  1320
tggagaccgg gagtgggatc atgacgggat ttgacatgtg ctgttgtcag ttgtgttatt  1380
tttaagggga gaacttcaga aacagaaaat agacacttag tcatatcaaa ctgtcaaaca  1440
agaagagaca catacacaca ttttctcaga gcgtgtcta gtgtgctacc ctaaaaaaaa   1500
tcaaatcaaa aattaaaata gaaatagaat agcgtttcta ctataatttg ctgttgttgt  1560
tattattatt atacctatta actagctaat                                   1590

<210> SEQ ID NO 2
<211> LENGTH: 1590
<212> TYPE: DNA
<213> ORGANISM: Kluyveromyces marxianus

<400> SEQUENCE: 2
catattagct agttaatagg tataataata ataacaacaa cagcaaatta tagtagaaac    60
gctattctat ttctatttta atttttgatt tgatttttt tagggtagca cactagacac   120
gcttctgaga aaatgtgtgt atgtgtctct tcttgtttga cagtttgata tgactaagtg   180 tctatttct gtttctgaag ttctcccctt aaaaataaca caactgacaa cagcacatgt   240
caaatcccgt catgatccca ctcccggtct ccatgtccca atgctcaaac acccatgtct   300
tttatatctt ttgcgctgcc cattttacaa agaaaccttg tacctttaaa aagtgatatg   360
acgaaaaaaa gaacaaatta aaaacagtg gggccctcca agaatcagt caataatcac    420 aaaacttaca ttacagcacg gcacagagcg catgccgcat agtagaaggg gagctacaga   480
agaagaaaaa aaaaaacaaa aaaaaacacta aggtaacgta aagtaagtat aataaaata   540 atctcatgag caccaccacc gctcgccgcg atatacaagg tgggatggga tgggattatt   600
ccaggatgtg gcggcgcggc gcggcgtagg aaagcagtag caagccggta ctagactgta   660
ctagactgta ctaactaacc ccagccgatc gccagctgga acaatggcat gcggggacgg  720
cccactgtgt tccgcgtaca cgtgatcaaa ttcggccgcg tactcccccgg gttcggacag  780 gtatggtccg tgcgcacccg gtgcactcca ccccgcgcgc ggcccactgc cttccggaaa   840
accaaaccaa aaaccaaaac caaaaccaaa aacaaagaaa ccaaaacaca tacctaaacc   900
acccagaaaa gcccgcgcaa gaaaccgttt ctcccccct ctctctgccc cgggtttcca   960
ggtattctca ctcaaggcat cccaattcca ggcttcgctt ctagcagcac ctgtggtgct  1020
gcttgctggt gtggtaccag cgtttcttta cgcctggcca ctgggcactg tgcgccgaaa  1080
cgcgcaagaa cagtagtagt agtggcacat tagcaagctt ttctgttgtg aatgtgattg  1140
```

```
atggatggat gattggcact ccatccgttc cttgcttacg caagctggca tatggcaatg    1200
tgtatgtgtg tgccccgaag tataggcagc taagcatatg atagttggct cgctctgcct    1260
ttgcagtgtc agatatacac agtatataag gagttgcctg aatcttgtca gccggttctt    1320
agaagtcttc agaaacactt tcgattcggg cacgttgtat aaataagtgt gttgtgtttc    1380
agtttggaga gagtgttgtt attactatta ttattattcg tgtgtatgtc catttgaaag    1440
tgtatatata tatatatatg tatatatgtc tggttagttt gtttgtctat aacaaccaaa    1500
aggtaaaata gtaatagtct ggagacccta aaagtatagg attccaagca aactagaaaa    1560
aaccaaaaaa acatcaagaa caatcaagaa                                     1590
```

<210> SEQ ID NO 3
<211> LENGTH: 1501
<212> TYPE: DNA
<213> ORGANISM: Kluyveromyces marxianus

<400> SEQUENCE: 3

```
gggaaaccaa atggaaccga gcaaagttga ccacttttga aaagaaaaaa agtattaaac      60
tttaacttaa cccgatgata tgattcgaat ttgatttact tgtcatgacc ccaccacgaa     120
accgcaatcc gctccttacg tttgatggtt tcgctttaat gaaataacaa accttaaaat     180
cccttttacc ccaataaaaa aaaactacaa ttataaaaaa gaaagatggg cagcaacgta     240
tgcatggact gctggaagcc atattatttg gttttgaaaa taataataat aataatatta     300
atattaatta aaaagcaccg cactggattt catagtgttc tctttcgccg gctgaattgg     360
catttgcttt ttaaatttac tcttcttatg acagcggtgc ttgtgttgtt gtcctcttta     420 ttttttttctt tcttcctttc actgccatca ttagcgttat tatatgctat tatgtctgtt     480
ctgctttctg aactcatata ttaagtaaaa aacacattta atattaaact agacataata     540
atctttagca tttcttcact tagtgtaata caatatacgg atacaattta atcaactata     600
tatttcttca tcacttattc ttgaatcctc cccgactttt tactcggcac cattgaaccg     660
tttattgctt caacctgtcg atcgatttat gcaagaaaag taatgcacaa cgcaatgcaa     720
agaggttgtt attgttcgga cggaaaaaca aaaacggagc ccgaatgtgc cacgtgattg     780
aagcccaatt aagaattacg tccgtgcggg gaaacacgga aaaggaaga gcaggaagaa     840 acggaaaaag ttcattccgg gaaaaagaaa actaaagca tagcgagaac aaaaaaaaac     900
aaaaacaaaa aaaactacat accgttttcg gcgcactgcg gtccacggtg gcccggaagg     960
cagtgttccg atccttggtc caccgcccgg aacgctccgg cccgaaacca tgcgatgagt    1020
ccagcttaca gctgaaacta caacggcccc cacacaactc tggcactggc tcatatatca    1080
cattaccatc agttggctgg ctggctggcg gacgggctat cgtatcgcat acgtagtttt    1140
cgctactgct actagcacaa ggccctaggc tggaaactgt gcactatgta taatgttgta    1200
tttttctatt agaagcttgt agataatact ggatgtgaag aacgtgtgac agcagatacc    1260
gaaagtgaac acacaaatgc gaattcaaga atacggtgca atataatgtt tgttaagtt    1320 ataaatttgt ataaattacc atgacatgga aactgaatcc aggttctttt gaaaactttc    1380
tctgtcgctt gcttactcga gcagtgtttt tttaggtaga caatacttaa acaaagcaca    1440
gcaaagtata acattgcata gcatagtata gccaagaaca aaaacataca ataaaataga    1500
a                                                                    1501
```

<210> SEQ ID NO 4
<211> LENGTH: 62

```
<212> TYPE: DNA
<213> ORGANISM: Artificial
<220> FEATURE:
<223> OTHER INFORMATION: URA3-5'40-KmGAL10c2

<400> SEQUENCE: 4
atcaaagaag gttaatgtgg ctgtggtttc agggtccata gagaaccaat gtaaccggca    60
cc                                                                  62

<210> SEQ ID NO 5
<211> LENGTH: 37
<212> TYPE: DNA
<213> ORGANISM: Artificial
<220> FEATURE:
<223> OTHER INFORMATION: 15G-KmGAL1+22c

<400> SEQUENCE: 5
gggggggggg ggggtgggc acaattggaa cggacat                             37
```